United States Patent [19]
Feierbach

[11] Patent Number: 5,935,078
[45] Date of Patent: Aug. 10, 1999

[54] TRANSDERMAL COMMUNICATION SYSTEM AND METHOD

[75] Inventor: Gary F. Feierbach, Belmont, Calif.

[73] Assignee: Telecom Medical, Inc., San Francisco, Calif.

[21] Appl. No.: 08/593,951

[22] Filed: Jan. 30, 1996

[51] Int. Cl.⁶ .............................. A61B 5/04; A61N 1/36
[52] U.S. Cl. ................... 600/509; 600/508; 607/32; 607/60; 128/903
[58] Field of Search .............................. 607/60, 31, 32; 128/903, 904; 600/508, 509

[56] References Cited

U.S. PATENT DOCUMENTS

| | | | |
|---|---|---|---|
| 4,166,470 | 9/1979 | Neumann | 607/33 |
| 4,543,953 | 10/1985 | Slocum et al. | |
| 4,571,589 | 2/1986 | Slocum et al. | |
| 4,958,645 | 9/1990 | Cadell et al. | |
| 5,205,204 | 4/1993 | Flach et al. | |
| 5,217,011 | 6/1993 | Bisch | |
| 5,218,207 | 6/1993 | Rosenthal | |
| 5,218,962 | 6/1993 | Mannheimer et al. | |
| 5,314,457 | 5/1994 | Jeutter et al. | 607/60 |
| 5,321,492 | 6/1994 | Detwiler et al. | |
| 5,360,437 | 11/1994 | Thompson | |
| 5,361,757 | 11/1994 | Smith et al. | |
| 5,368,040 | 11/1994 | Carney | |
| 5,383,467 | 1/1995 | Auer et al. | |
| 5,383,912 | 1/1995 | Cox et al. | |
| 5,383,915 | 1/1995 | Adams | 607/60 |
| 5,387,259 | 2/1995 | Davidson | |
| 5,391,190 | 2/1995 | Krueger et al. | |
| 5,626,630 | 5/1997 | Markowitz et al. | 607/60 |
| 5,630,836 | 5/1997 | Prem et al. | 607/60 |

*Primary Examiner*—William E. Kamm
*Assistant Examiner*—Carl H. Layno

[57] ABSTRACT

A transdermal communication system is disclosed. The system includes an internal communication device implanted inside the body of a patient and an external communication device. The external communication device includes an external transmitter which transmits a carrier signal into the body of the patient during communication from the internal communication device to the external communication device. The internal communication device includes an internal modulator which modulates the carrier signal with information by selectively reflecting the carrier signal or not reflecting the carrier signal. The external communication device demodulates the carrier signal by detecting when the carrier signal is reflected and when the carrier signal is not reflected through the skin of the patient. When the reflected carrier signal is detected, it is interpreted as data of a first state, and when the reflected carrier signal is not detected, it is interpreted as data of a second state. Accordingly, the internal communication device consumes relatively little power because the carrier signal used to carry the information is derived from the external communication device. Further, transfer of data is also very efficient because the period needed to modulate information of either the first state or the second state onto the carrier signal is the same.

34 Claims, 5 Drawing Sheets

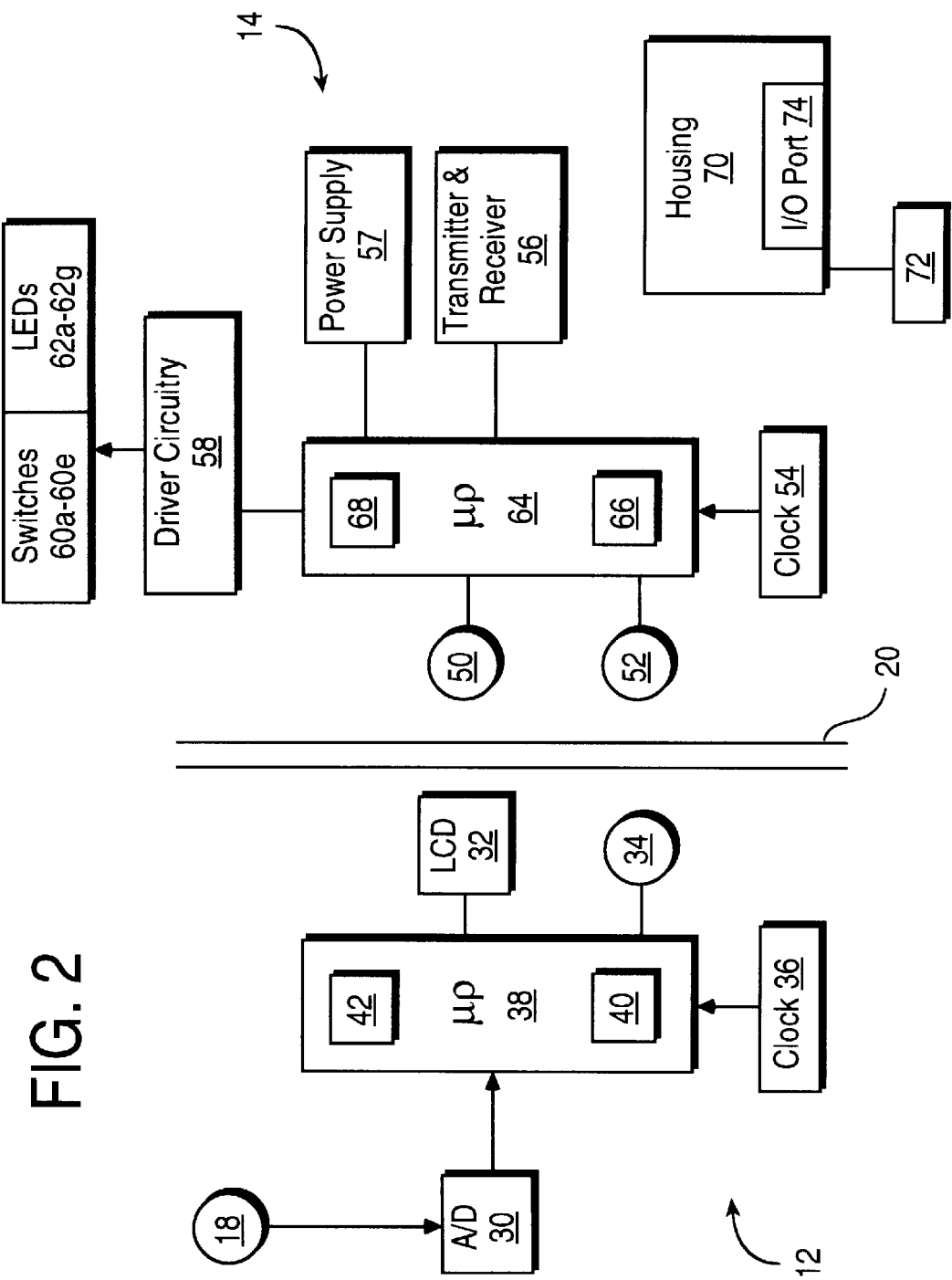

Carrier Signal $t_0$ $t_1$ $t_2$ $t_3$ $t_4$ $t_5$ $t_6$ $t_7$ $t_8$ $t_9$ $t_{10}$ $t_{11}$ Reflected Signal $t_0$ $t_1$ $t_2$ $t_3$ $t_4$ $t_5$ $t_6$ $t_7$ $t_8$ $t_9$ $t_{10}$ $t_{11}$

TRANSDERMAL COMMUNICATION SYSTEM AND METHOD

CROSS REFERENCE TO RELATED APPLICATIONS

Copending U.S. patent application Ser. No. 08/549,375, entitled "System and Method to Monitor the Heart of a Patent", filed Oct. 27, 1995, which is a continuation-in-part application of U.S. patent application Ser. No. 08/545/306, entitled "System and Method to Measure to the Condition of a Patent's Heart", filed Oct. 19, 1995, both assigned to the assignee of the present invention, are incorporated by reference herein.

BACKGROUND OF THE INVENTION

1. Field of the Invention

The present invention relates to a transdermal communication system having an internal communication device and an external communication device, and more particularly, to a transdermal communication system wherein data stored in the body is transferred to the external communication device by modulating a carrier signal, transmitted by the external communication device, with the data by either reflecting the carrier signal or not reflecting the carrier signal, and recovering the data at the external communication device by detecting when the carrier signal is either reflected or not reflected.

2. Background Art

With recent advances in the field of microelectronics, it is now common to subdermally implant semiconductor chips and related circuitry into the body of a patient. The chips and circuitry are used to control a variety of bodily functions, and/or monitor anyone of a number of physiological attributes of a patient. For example, U.S. Pat. No. 5,391,190 entitled "Variation in Cardiac Chamber Volume or Pressure as a Controlling Parameter" issued to Pederson on Feb. 21, 1995, discloses the use of a cardiac pacemaker system that uses a subdermally implanted microprocessor to control the heart beat rate of the patient based on a heart and respiratory measurement. In yet another example, Carney in U.S. Pat. No. 5,368,040 entitled "Apparatus and Method for Determining A Plurality of Hemodynamic Variables From A Single Chronically Implanted Absolute PressureSensor", issued Nov. 29, 1994, discloses a telemetry system wherein circuitry subdermally implanted into a patient is used to transmit blood pressure measurements to a receiver external to the body.

One problem confronting bio-medical engineers developing transdermal communication devices is providing electrical power to the chronically implanted circuitry inside the body. The majority of implanted devices are powered using a battery. The power of the battery eventually drains, and needs to be replaced. The most common way to replace the battery is through surgery. Prior to the expiration of the battery, an operation is performed on the patient and either the battery is replaced, or a new device is implanted into the patient. Surgery, however, is usually a major ordeal for the patient, is costly, and is generally undesirable. Another way to provide power to an implanted device is through the use of a split transformer, where one coil of the transformer is located underneath the skin and the other coil is positioned outside the skin. The transformer is used to replenish power to an implanted power supply, such as a battery, when needed. See for example the above referenced Carney patent. The problem with transformers is that they require a coil to be implanted under the skin. The implanted coil is typically bulky, and the spilt transformer provides relatively little power transfer to the internal device.

Another problem confronting biomedical engineers is providing two-way communication through the skin of the patient. It is known to surgically implant wires through the skin of the patient. While this approach facilities two-way communication, it is generally undesirable. Chronically implanted wires piercing the skin tend to be uncomfortable for the patient, are unsanitary, and may cause infection. Radio telemetry is another known approach for communicating between an implanted device and an external device. With radio telemetry, data is transmitted either into or out of the body using radio waves. The problem with radio telemetry is that a transmitter/receiver is needed inside the body of the patient. These transmitter/receivers tend to be very sophisticated and expensive. Furthermore, the transmitter/receiver inside the body consumes a relatively large amount of power, particularly during broadcasting. In battery powered radio telemetry transdermal communication devices, the frequent broadcasting of data from the body to an external receiver tends to significantly reduce the life of the battery.

U.S. Pat. No. 5,387,259 entitled *"Optical Transdermal Linking Method for Transmitting Power and Receiving an Internal Data Stream While Receiving a Second Data Stream,"*, issued to Davidson on Feb. 7, 1995, discloses an optical transdermal system. The system of Davidson provides an internal module implanted underneath the skin of a patient, and an external module. The internal module includes a photodetector, a preamplifier, a clock recovery circuitry for detecting an incoming optical signal, a laser diode and driver for transmitting an optical signal, and a photo-cell for providing power to the internal module. The external module includes one or more laser diodes for transmitting an optical signal to the internal module, and a photodetector for receiving an optical signal from the internal module. Davidson teaches two ways in which power can be provided to the internal module. One way is to provide the external module with an unmodulated laser diode which is dedicated for power transmission and a second laser diode dedicated for data transmission. Alternatively, a single laser diode can be used for both power transmission and data transmission. Regardless of the number of laser diodes used in the external module, the photo-cell of the internal module absorbs light transmitted through the skin of the patient by the laser diode of the external module. The light energy is then converted to electrical energy for powering the internal module.

A problem associated with the system of Davidson is that it requires the transmission of a relatively high power optical energy signal into the body to provide and replenish power to the internal module. The internal module also requires a photo-cell to convert the light energy into electrical energy. This process is generally inefficient, particularly through the skin and tissue of the patient. The internal module is also required to drive its own laser diode when transmitting data external to the body. Laser diodes consume a relatively large amount of power, which tends to drain the power of the photo-cell. Consequently, the Davidson device is less than ideal because the patient would be required to repeatedly replenish the photo-cell of the internal module.

U.S. Pat. No. 4,571,589 entitled *"Biomedical Implant with High Speed, Low Power Two Way Telemetry"*, issued to Slocum on Feb. 18, 1986 discloses a transdermal communication system that relies on an external coil and an internal coil implanted under the skin of a patient. During data transmission from inside to outside of the body, the external coil generates a 64 KHz carrier signal. The impedance of the internal coil is then modulated using a switch. For example, in transmitting a binary zero, the carrier signal is modulated for two cycles. With a binary one, the carrier is modulated for six cycles. The modulated carrier signal is then re-radiated by the internal coil to the external coil. The re-radiated signal is then demodulated to recover the transmitted data by measuring the length of time in which the impedance of the internal coil modulated by the switch. The problem with this arrangement is that modulation of the data, particularly a binary one, takes up to six cycles. As a result, the data transfer from the internal to external communication device is relatively inefficient.

Accordingly, a transdermal communication system is needed wherein the energy required for communication between the internal and external communication devices is substantially provided by the external communication device and wherein the data transfer from the internal communication device to the external communication device is efficient.

SUMMARY OF THE INVENTION

The present invention relates to a transdermal communication system. The system includes an internal communication device implanted inside the body of a patient and an external communication device. The external communication device includes an external transmitter which transmits a carrier signal into the body of the patient during communication from the internal communication device to the external communication device. The internal communication device includes an internal modulator which modulates the carrier signal with information by selectively reflecting the carrier signal or not reflecting the carrier signal. The external communication device demodulates the carrier signal by detecting when the carrier signal is reflected and when the carrier signal is not reflected through the skin of the patient. When the reflected carrier signal is detected, it is interpreted as data of a first state, and when the reelected carrier signal is not detected, it is interpreted as data of a second state. Accordingly, the internal communication device consumes relatively little power because the carrier signal used to carry the information is derived from the external communication device. Further, transfer of data is also very efficient because the period needed to modulate information of either the first state or the second state onto the carrier signal is the same.

DESCRIPTION OF THE DRAWINGS

The features and advantages of the present invention will be apparent from the following description in which:

FIG. 2 is a logic diagram of an internal communication device and an external communication device of the present invention.

DESCRIPTION OF THE PREFERRED EMBODIMENT

Figure 1:
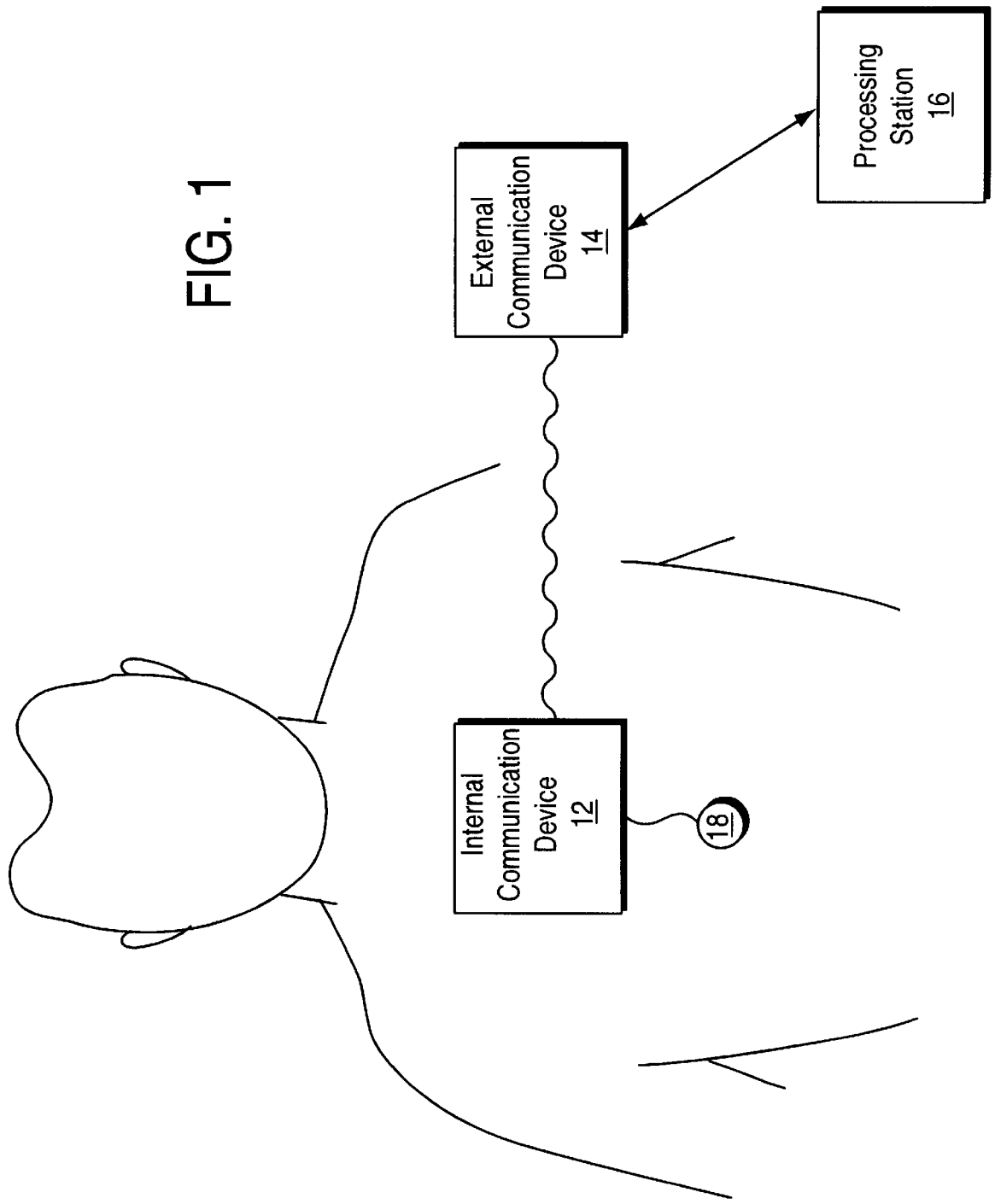
FIG. 1 is a block diagram of the transdermal communication device of the present invention.

Referring to FIG. 1, a block diagram of a transdermal communication device of the present invention is shown. The communication device 10 includes an internal communication device 12, an external communication device 14, and a processing station 16. The internal communication device 12 is coupled to a measuring device 18. The internal communication device 12 and the measuring device 18 are both implanted in the body of a patient. According to various embodiments of the invention, the measuring device 18 measures any physiological attribute of the patient, and generates an absolute signal indicative of the measured attribute. The internal communication device 12 receives the absolute signal and performs one or more data processing operations on the absolute signal. The internal communication device 12 then temporarily stores the processed data. Upon the direction of the patient, the internal communication device 12 transfers the stored data to the external communication device 14 through the skin of the patient. The external communication device 14 transfers the processed data to the processing station 16, where the data is further processed and analyzed. The processing station 16 presents the data related to the measured physiological attribute to a doctor or other medical personnel, who then may monitor the physiological attribute of the patient, and may subscribe a treatment for the patient if needed. The external communication device 14 can also be used to communicate information from the processing station 16 to the internal communication device 12. Such information may include a computer program used to control the internal communication device 12, updates to a computer program previously stored in the internal communication device 12, or control information directing the internal communication device 12 to sample the absolute signal at a specific time or times.

In one embodiment, the measuring device 18 is a blood pressure sensor implanted into the heart of the patient. The blood pressure sensor generates a signal indicative of the absolute blood pressure in the heart of the patient. The internal communication device 12 contains circuitry that samples the absolute blood pressure signal, and generates a filtered blood pressure signal in response thereto. The circuitry in the internal communication device 12 then analyzes the filtered blood pressure signal, and then generates a set of parameters indicative of the condition and strength of the heart of the patient. The set of parameters are then temporarily stored in the internal communication device 12. The set of parameters are then subsequently transferred to the external communication device 14, and the processing station 16 for further processing and analysis. For more information regarding this embodiment, see the above mentioned application Ser. No. 08/545,306. In alternative embodiments, the circuitry of the internal communication device 12 may be used to process, filter and generate parameters for any physiological attribute of the patient. Such physiological attributes may include, but are not limited to, ecg, chemical, hormonal, digestive, neural, or any organ in the body including, but not limited to, the brain, heart, lungs, kidneys, liver, blood, bladder, etc.

Referring to FIG. 2, a logic diagram of the internal communication device 12 and the external communication device 14 is shown. The internal device 12 and the external device 14 are separated by the skin 20 of the patient.

The internal communication device 12 includes an analog to digital (A/D) converter 30, a liquid crystal display (LCD)

32, a photodetector 34, a clock 36, and a microprocessor 38. The microprocessor 38 includes a programmable memory 40 for storing microcode used to control the operation of the microprocessor 40, and a static random access memory (SRAM) 42 for storing processed data and other information generated by the microprocessor 38. The A/D converter samples and digitizes the absolute signal generated by the measuring device 18. The microprocessor 38 receives the digitized samples, and processes them in accordance with the program stored in the programmable memory 40. The processed data is then stored in the SRAM 42. The clock 36 generates a clock signal to drive the microprocessor 38. In some embodiments, the clock 38 also provides the microprocessor 38 with "time of day" information. The time of day information enables the internal communication device 12 to "wake up" and sample the absolute signal, process the signal, and store the resulting data in the SRAM 42 at a predesignated time or times. The LCD 32 is used to transmit the data stored in the SRAM 42 to the external communication device 14. The photodetector 34 is used to receive information from the external communication device 14 and provide it to the microprocessor 38.

In one embodiment, the A/D converter 30 can be anyone of a number of commercially available converters capable of sampling the absolute signal at least one hundred and twenty times per second. The LCD 32 is custom made by the Polytronics, Inc., and has a single LED element, as opposed to most other commercially available LEDs which have multiple active LED elements. The photodetector 34 is a Darlington type photo diode such as model number 3035A by the NDE Corporation, Bloomfield, N.J. The clock 36 is any one of a number of commercially available clock chips, such as from the Seiko Corporation, Japan. The microprocessor 38 is model number PIC1671 by the Microchip Corporation, Chandler, Ariz. In alternative embodiments, the SRAM 40 may be replaced or augmented with any programmable memory, such as flash memory or EEPROM. Similarly, the memory 40 storing microcode can be replaced by control circuitry, or a combination of microcode and control circuitry, used to control the microprocessor 38. Furthermore, the functionality of the A/D converter 30, the LCD 32, the photodetector 34, the clock chip 36, and the microprocessor 38 can be combined into one or more integrated circuits. It should be noted that the above elements are only exemplary, and that elements with similar functions may be used.

The external communication device 14 includes a light emitting diode (LED) 50, a photodetector 52, a clock 54, a transmitter/receiver 56, a rechargeable power supply 57, driver circuitry 58 for driving several switches 60a through 60e and LEDs 62a through 62g, and a microprocessor 64. The microprocessor contains programmable memory 66 for storing microcode used for controlling the microprocessor 64, and flash memory 68 for temporarily storing information. The information stored in the flash memory 68 may be either the processed data down-loaded from the internal communication device 12, or information from the processing station 16 temporarily stored in the external communication device 14 before it is up-loaded to the internal communication device 12.

In one embodiment, the LED 50 is a standard LED which is red in color. The photodetector 52 is model number NTE303JA by the NDE Corporation. The clock 54 is any commercially available clock chip, such as that from the Seiko Corporation. The microprocessor 64 is model number 68HC11FN from Motorola. The memory 66 storing microcode can be replaced by control circuitry, or a combination of microcode and control circuitry, used to control the microprocessor 64. Furthermore, functionality of the LED 50, photodetector 52, the clock 54, and the microprocessor 62 can be combined into one or more integrated circuits. It should be noted that the above elements are only exemplary, and that elements with similar functions may be used.

A housing 70 is provided to store the external communication device 14. The housing is coupled to a power supply 72 which is used to recharge the rechargeable power supply 57 when the external communication device 14 is housed in the housing 70. The housing 70 also includes an input/output (I/O) port 74. The I/O port 74 is used to couple the transmitter/receiver 56 of the external communication device 14 to the processing station 16. In accordance with one embodiment, the transmitter/receiver 56 is a modem, and the I/O port 74 is a telephone jack. In another embodiment, the transmitter/receiver 56 and I/O port 74 form an interface node of a computer network. The external communication device 14 is capable of transmitting and receiving information through the interface node to and from the processing station 16 located at an external node on the network. In yet another embodiment, the transmitter/receiver 56 is a radio transmitter/receiver capable of two-way communication with the processing station 16.

The switches 60a through 60e are used to control the operation of the transdermal communication device 10. The function of each of the switches 60a through 60e is provided in Table I below.

TABLE I

| SWITCH | FUNCTION |
|---|---|
| 60a | This switch turns the external communication device 14 ON or OFF |
| 60b | When activated, this switch causes the external communication device 14 to generate a first predefined string of bits which informs the internal communication device 12 to prepare to receive information from the external communication device 14. |
| 60c | When activated, this switch causes the external communication device 14 to generate a second predefined string of bits which informs the internal commuincation device 12 to prepare to transmit information to the external communication device 14. |
| 60d | When activated, this switch initiates data transfer from the external communication device 14 to the processing station 16. |
| 60e | When activated, this switch directs the external communication device 14 to transmit a third predefined string of bits used for alignment. |

The LED indicators 62a through 62g are used to inform the patient of the status of key features of the external communication device 14. The function of each of the indicators 60a through 60g provided in Table II below.

TABLE II

| LED | FUNCTION |
|---|---|
| 62a | This LED indicates if the external communication device 12 is ON/OFF. |
| 62b | This LED indicates if the rechargeable power supply 57 is charged or charging. |
| 62c | This LED indicates if the external communication device 14 is transmitting or receiving information from the processing station 16. |
| 62d | This LED informs the patient that it is time to down load the information stored in the internal communication device 12 to the external communication device 14. In alternative embodiments, this LED may be replaced with an audio signal, such as an alarm or a chime. |
| 62e | This LED indicates that data is being transferred from the external communication device 14 to the internal communication device 12. |
| 62f | This LED indicates that data is being transferred from the internal communication device 12 to the external communication device 14. |
| 62g | This LED indicate that the external communication device 14 is properly aligned with the internal communication device 12 located under the skin of the patient. |

Figure 3A:
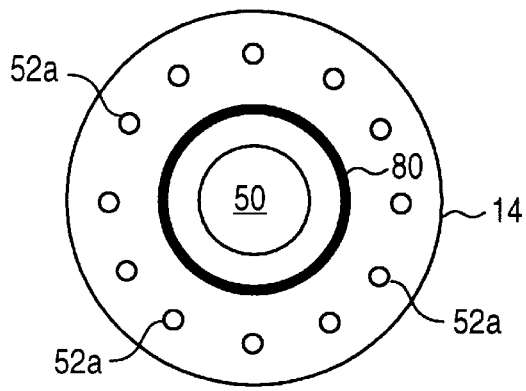
FIGS. 3A through 3C are three views of the external communication device according to three embodiments of the present invention respectively.
Figure 3B:
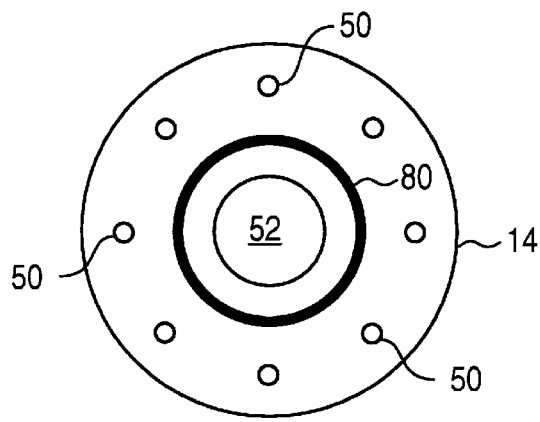
Figure 3C:
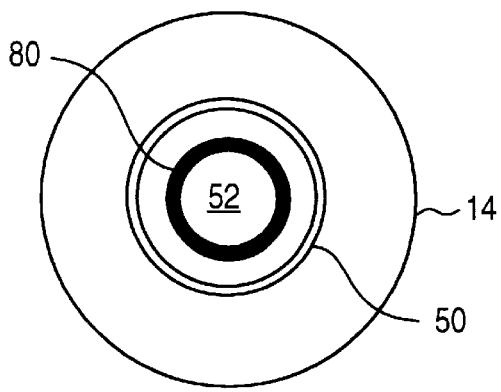

Referring to FIGS. 3A through 3C, three possible embodiments of the external communication device according to the present invention is shown. In FIG. 3A, the LED 50 is positioned at the center of the external communication device 14, and a set of photodetectors 52 are arranged around the LED 50. An opaque ring 80 is positioned between the LED 50 and photodetector 52. In FIG. 3B, the photodetector 52 is positioned at the center of the external communication device 14, and eight LEDs 52 are arranged around the photodetector 52. In this embodiment, the LEDs are red in color, and are in the range of ten to twenty millicandles. An opaque ring 80 is positioned between the LEDs 50 and photodetector 52. In FIG. 3C, the LED 50 is positioned at the center of the external communication device 14, and a ring photodetector 52 is arranged around the LED 50. An opaque ring 80 is positioned between the LED 50 and photodetector 52. In yet another embodiment (not shown), the photodetector 52 can be placed in the center of the external communication device 14, and a ring LED 50 is arranged around the photodetector 52. An opaque ring so is positioned between the LED and photodetector 52. It should be noted that FIGS. 3A through 3C are only exemplary, and any number of different configurations for the LED 50 and the photodetector 52 may be used. Regardless of the actual configuration, the LCD 32 and the photodetector 34 of the internal communication device 12 is configured to "mirror" that of the external communication device 14.

OPERATION

When the external communication device 14 is not in use, it is stored in the housing 70. The switch 60a is placed in the OFF position, and, as a result, the LED 62a is not activated. The rechargeable power supply 57 of the external communication device 14 is recharged by the power supply 72 if needed. The LED 62b indicates if the rechargeable power supply is charged or charging.

The external communication device 14 is capable of receiving information from the processing station 16 when stored in the housing 70. When the processing station 16 sends the external communication device 14 information, the LED 62c is activated, indicating that the external communication device is communicating with the processing station 16 and should not be removed from the housing 70. As previously noted, the information received may include control information used to control the internal communication device 12, information to update the program stored in the internal communication device 12, or a message for the patient. For example, medical personnel at the processing station 16 may desire that data stored in the internal communication device 12 to be transferred to the processing station 16 immediately. In which case, the medical personnel, through the processing station 16, may send a message to the external communication device 14, which in turn, activates the LED 62d. In response, the patient performs the down-loading operation when the LED 62d is activated. Alternatively, the external communication device 14 may be programmed to activate the LED 62d at a specific time or times each day to remind the patient to perform the down-loading operation.

When information in the external communication device 14 is to be up-loaded to the internal communication device 12, the external communication device is removed from the housing 70 and turned on by switch 60a. The internal communication device 12 and the external communication device 14 are then aligned through the skin 20 of the patient. When alignment is achieved, the patient activates switch 60b, causing the first predefined string of bits to be transmitted into the body. The first predefined string of bits prepares the internal communication device 12 to receive information. The LED 50 of the external communication device then transmits the information stored in the memory 68, under the direction of the microprocessor 64, in the form of encoded light signals through the skin 20 of the patient. The photodetector 34 of the internal communication device 12 receives the encoded light signals, and provides them to the microprocessor 38, where they are decoded. According to various embodiments of the invention, a number of different encoding schemes may be used, such as non-return to zero (NRZ), NRZI, DFR, Bi-phase M, Bi-Phase L, or any other encoding scheme, during data transmission. The LED 62e is activated when up-loading operation is taking place, and is de-activated when the complete.

When information in the internal communication device 12 is to be down-loaded to the external communication device 14, the external communication device is removed from the housing 70 and turned on by switch 60a. The internal communication device 12 and the external communication device 14 are then aligned. Once alignment is achieved, the patient then activates the switch 60c, causing the second predefined string of bits to be transmitted into the body. The second predefined string of bits instructs the microprocessor 38 to transmit the information stored in SRAM 42 to the external communication device 14. This is accomplished by the microprocessor 64 of the external communication device 14 in cooperation with the microprocessor 38 of the internal communication device 12. The LED 62f is activated when data is being down-loaded from the internal communication device 12 to the external communication device 14.

Figure 4:
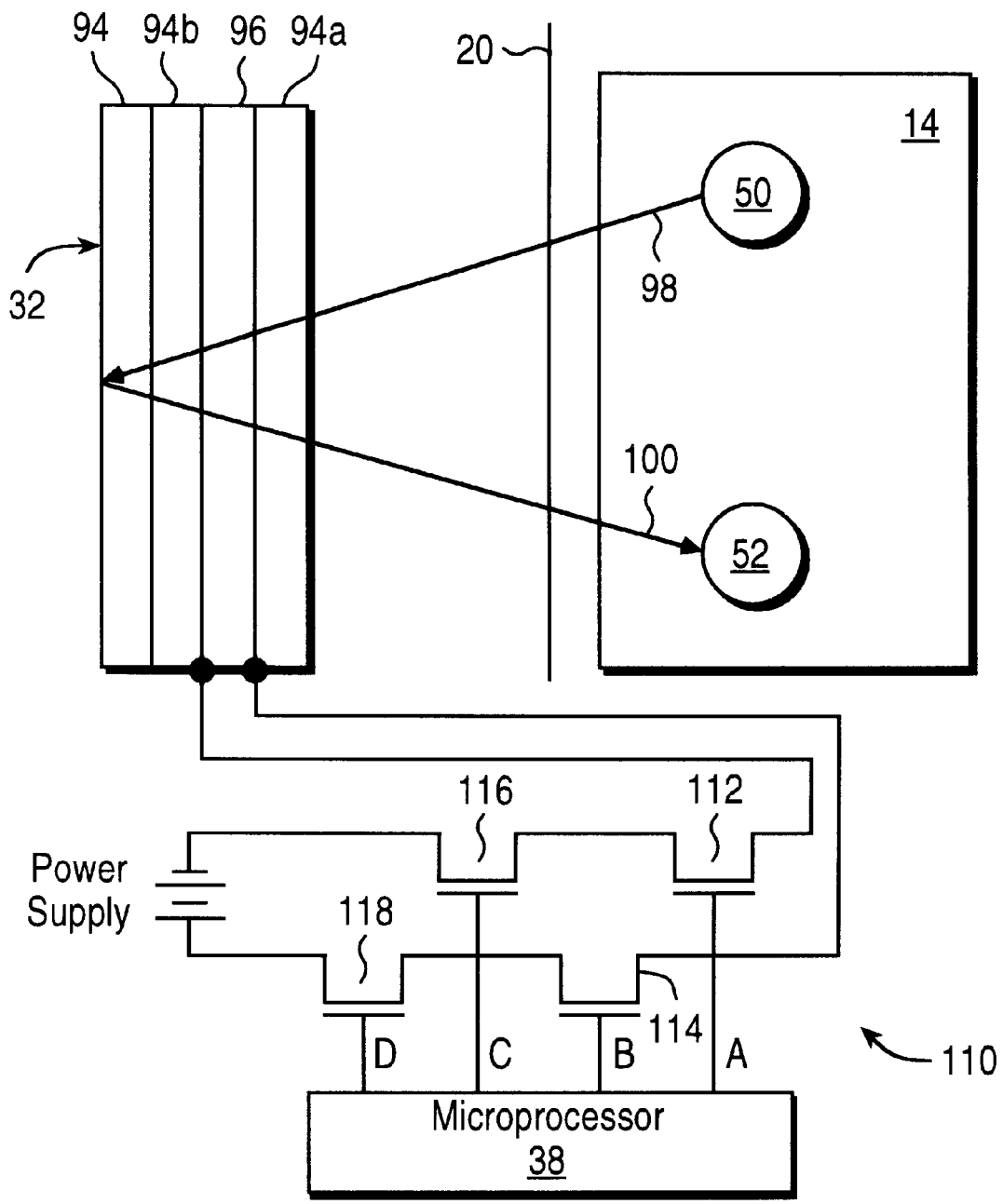
FIG. 4 illustrates a control circuit for a liquid crystal display used for transmitting data from the internal communication device to the external communication device according to the present invention.

Referring to FIG. 4, a diagram of a control circuit for controlling the LCD 32 of the internal communication device 12 is shown. The LCD 32 includes a mirror layer 92, transparent glass layers 94a and 94b, and and liquid crystal layer 96. A control circuit 110, coupled between the microprocessor 38 and the LCD 32. The control circuit includes four N-channel MOSFET transistors 112, 114, 116, and 118 configured as shown. The gates of the four transistors 112, 114, 116, and 118 are coupled to outputs A, B, C and D of microprocessor 38 respectively. The microprocessor 38 uses the four signals A, B, C, and D to transition the LCD 32 between the opaque state and the transparent state. The microprocessor 38 activates all four transistors 112, 114, 116, and 118 by driving the signals A, B, C and D to a high level to transition the LCD 32 into the transparent state. When transitioning the LCD into the opaque state, the microprocessor 38 alternatively driving signals A and B high and C and D low, or vice versa, to prevent the LCD 32 from polarizing.

The liquid crystal layer 96 is capable of switching between a transparent state (ON) or an opaque state (OFF). The liquid crystal layer 96 is coupled to and controlled by the microprocessor 38 and the control circuit 110. When data is to be down-loaded, the microprocessor 64 of the external communication device 14 causes the LED 50 to turn on and off at a high frequency, resulting in a carrier signal 98 being transmitted into the patient. The microprocessor 38 of the internal communication device 12 modulates the carrier signal 98 with the data stored in the SRAM 42 by switching the LCD 32 between the transparent and opaque state. For example, when transmitting a logical one, the LCD 32 is placed in the transparent state, and the photodetector 52 of the external communication device 14 receives a reflected carrier signal 100 reflected off the mirrored layer 92 of the LCD 32. On the other hand, when transmitting a logical zero, the crystal layer 96 of the LCD 32 is made opaque. The photodetector 52 therefore does not receive the reflected carrier signal 100 during the transmission of a logical zero. In this manner, the information contained in the SRAM 42 of the internal communication device 12 is transmitted to the external communication device 14 through the skin of the patient. The reflected carrier signal 100 is modulated in accordance with any of the above-mentioned encoding schemes.

Figure 5A:
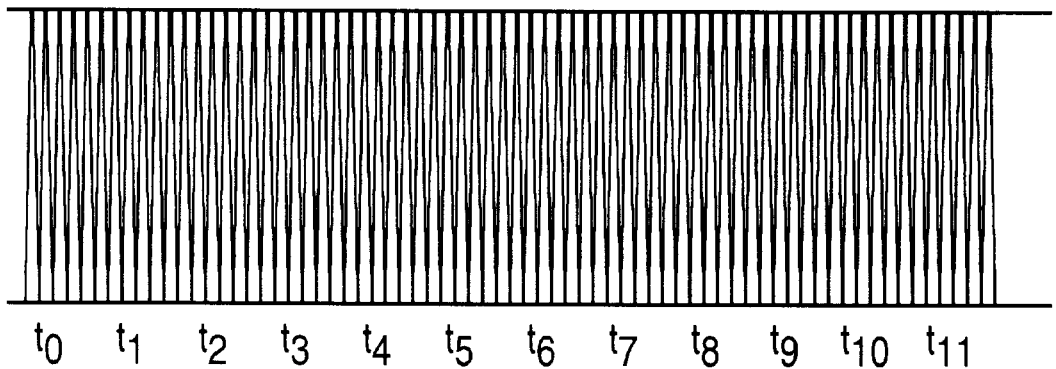
FIG. 5 illustrates a carrier signal transmitted into the body of the patient and a reflected carrier signal according to the present invention.
Figure 5B:
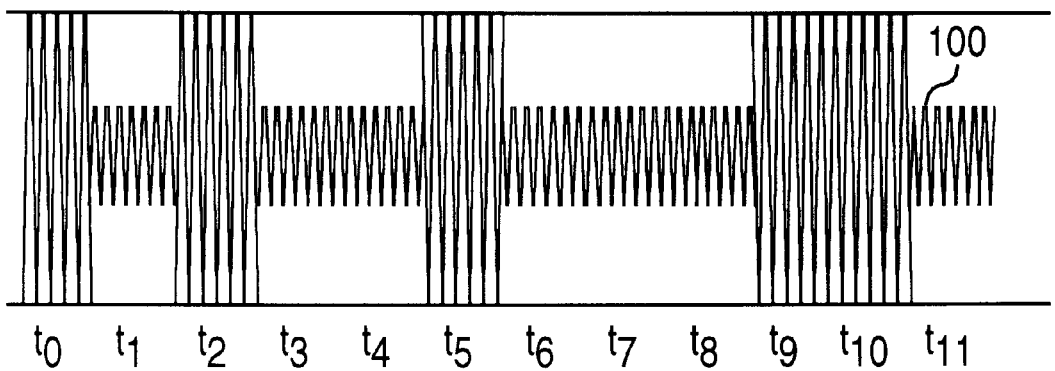

Referring to FIG. 5, a signal 98 as transmitted by LED 50 and a reflected into the body of the patient and a reflected carrier signal 100 as reflected by LCD 32 is shown. In one embodiment, the frequency of carrier signal 98 is 5 KHz or greater. The Table III below provides the DATA transferred (either a "1" for logical one or a "0" for logical zero) external to the body and the STATE of the LCD 32 (either "T" for transparent or "O" for opaque) for eleven time intervals $t_0$ through $t_{10}$ respectively as illustrated in figure.

TABLE III

| Time Interval | $t_0$ | $t_1$ | $t_2$ | $t_3$ | $t_4$ | $t_5$ | $t_6$ | $t_7$ | $t_8$ | $t_9$ | $t_{10}$ |
|---|---|---|---|---|---|---|---|---|---|---|---|
| DATA | 1 | 0 | 1 | 0 | 0 | 1 | 0 | 0 | 0 | 1 | 1 |
| STATE | T | O | T | O | O | T | O | O | O | T | T |

Once the down-load operation has been completed, the data needs to be transferred to the processing station 16. Data can be transferred to the processing station either automatically, at a pre-designated time, or upon the direction of the patient. For example, the clock 54 of the external communication device 14 may be used to inform the microprocessor 64 to transmit the data through the transmitter/receiver 56 to the processing station at a specific time or times each day. Alternatively, the patient can over-ride the automatic transmission feature, and direct the microprocessor 64 to transmit the data on command. To initiate this feature, the patient is required to activate switch 60d, which causes the data stored in the microprocessor 68 to be transferred to the processing station 16 through the transmitter receiver 56.

The external communication device 14 and the internal communication device 12 need to be properly aligned before correct data communication can take place. To achieve alignment, the patient places the external communication device 14 in the relative proximity of the internal communication device 12 located beneath the skin of the patient. The patient subsequently activates switch 60e, which causes the external communication device 14 to transmit the third predefined string of bits into the body of the patient. The internal communication device 12 reads the third predefined string of bits, and compares it with a designated string of bits stored in the microprocessor 38. The external communication device 14 then transmits a carrier signal 98 into the patient. The internal communication device 12, using the same method as described above, modulates the carrier signal 98, and transmits a reflected carrier signal 100 with the third predefined string of bits modulated thereon back to the external communication device 14. If the bit string transmitted and received by the external communication device 14 is the same, then the two communication devices 12 and 14 are aligned. If a mis-match occurs, the patient is required to adjust the position of the external communication device 14, and to repeat the alignment steps, until a match occurs. In one embodiment, a visible marker, such as a tattoo or other designator, may be used to help the patient align the two communication devices. When alignment is achieved, the LED 62g, or alternatively an audio signal such as a chime, is activated informing the patient that it is permissible for either an up-loading or a down-loading operation to take place.

With the present invention, the majority of the energy required for communication between the internal communication device 12 and the external communication device 14 is supplied by the external communication device 14. Since the internal communication device 12 uses very little energy, the battery life of the device is conserved. Further, since the time period required to modulate both a logical one and a logical zero are both one clock cycle t, the rate of data transfer is improved. While the present invention has been described in relationship to the embodiments shown in the accompanying figures, other alternatives, modifications and embodiments will be apparent to those skilled in the art. For example, high frequency carrier signal 98 can be replaced with a DC carrier signal. Transdermal communication can also be accomplished by other forms of energy besides light, such as RF, sound, or any other type of energy. Some or all of the LEDs 62a through 62e can be replaced by an audio signal, such as an alarm or a chime. Further, some of the functionality and associated circuitry of the of the switches 60a through 60e can be moved to the housing 70. It is intended that the specification be only exemplary, and that the true scope and spirit of the invention be indicated by the following claims.

I claim:

1. A transdermal communication system; comprising:
    an internal communication device configured to be implanted inside the body of a patient;
    an external communication device configured to be located outside the body of the patient;
    an external transmitter, coupled to the external device, and configured to transmit a carrier signal into the body of the patient during communication from the internal communication device to the external communication device;
    an internal modulator, coupled to the internal communication device, and configured to modulate the carrier signal with information by selectively reflecting the carrier signal or not reflecting the carrier signal, the internal modulator configured to modulate the carrier signal with information of a first state during a first time interval during which the carrier signal is reflected and to modulate the carrier signal with information of a second state during a second time interval during which the carrier signal is not reflected; and an external demodulator, coupled to the external communication device, and configured to demodulate the carrier signal by detecting when the carrier signal is reflected and when the carrier signal is not reflected.

2. The system of claim 1, wherein the first time interval and the second time interval have substantially the same duration.

3. The system of claim 1, wherein the internal modulator is a liquid crystal display including a reflective surface which is configured to reflect the carrier signal received from the external transmitter when modulating the carrier signal with the information of a first state.

4. The system of claim 1, wherein the internal modulator is a liquid crystal display which includes a crystal element configured to be opaque to prevent reflection of the carrier signal from the external transmitter when modulating the carrier signal with the information of a second state.

5. The system of claim 1, wherein the internal modulator modulates the carrier signal in accordance with a predefined encoding scheme.

6. The system of claim 1, further comprising a transmitter/receiver, coupled to the external communication device, and configured to transmit the information demodulated from the carrier signal received at the external demodulator to a processing station.

7. The system of claim 6, wherein a communication medium is coupled between the transmitter/receiver and the processing station.

8. The system of claim 7, wherein the communication medium comprises one communication medium among the following group of communication mediums: radio waves; telephone lines; or a computer network.

9. The system of claim 1, further comprising an alignment element, the alignment element configured to align the internal communication device when implanted beneath the skin of the patient and the external communication device located outside the body of the patient.

10. The system of claim 9, wherein the alignment element further comprises:

an external processor, included in the external communication device, and configured to instruct the external transmitter to transmit a predefined signal into the body of the patient;

an internal receiver, included in the internal communication device, to receive the predefined signal;

an internal compare element, included in the internal communication device, to compare the predefined signal received by the internal receiver with a pre-stored signal stored in the internal communication device; and an indicator, coupled to the external communication device, to indicate that the internal communication device and the external communication device are aligned when the internal compare element determines that the predefined signal received by the internal receiver and the pre-stored signal match.

11. The system of claim 1, wherein the external communication device further comprises an external processor, the external processor coupled to the external transmitter, the external processor configured to instruct the external transmitter to transmit the carrier signal into the body of the patient.

12. The system of claim 1, wherein the external communication device further comprises an external memory configured to store the information demodulated from the carrier signal by the external demodulator.

13. The system of claim 12, further comprising an external clock circuit, coupled to an external processor, the external clock circuit configured to provide the external processor with timing data so that the external processor can down-load the information stored in the external memory to a processing station at a designated time.

14. The system of claim 12, further comprising a data transmission switch, coupled to an external processor, the data transmission switch configured to instruct the external processor to down-load the information stored in the external memory to a processing station when the data transmission switch is activated.

15. The system of claim 1, wherein the external transmitter comprises a light emitting diode.

16. The system of claim 1, wherein the external communication device further comprises an external photodetector configured to receive the carrier signal reflected from the internal modulator.

17. The system of claim 1, further comprising a housing configured to store the external communication device.

18. The system of claim 17, wherein the housing further comprises a rechargeble power supply.

19. The system of claim 1, further comprising an indicator, coupled to the external communication device, to indicate when the internal communication device and the external communication device are communicating.

20. The system of claim 1, wherein the internal communication device further contains an internal processor coupled to a measuring device configured to be implanted into the body of the patient, the measuring device configured to measure a predefined physiological attribute of the patient and to generate an absolute physiological attribute signal in response thereto, the internal processor further configured to generate the information used to modulate the carrier signal received from the external communication device by processing the absolute physical attribute signal.

21. The system of claim 20, further comprising an internal clock element, coupled to the internal processor, the internal clock element configured to provide the internal processor with timing information so that the internal processor can sample the absolute physiological attribute signal and process the sampled absolute physiological attribute signal at a pre-designated time.

22. The system of claim 20, further comprising a processing station, coupled to the external communication device, the processing station and the internal communication device configured to communicate through the external communication device.

23. The system of claim 22, wherein the processing station provides the internal communication device with timing information to control the time the internal processor processes the absolute physiological attribute signal.

24. The system of claim 22, wherein the processing station provides the internal communication device with control information to control the internal processor.

25. The system of claim 1, wherein the internal communication device further further comprises an internal photodetector configured to receive encoded data from the external communication device.

26. The system of claim 1, wherein the external transmitter is an LED and the external modulator comprises a photodetector and a processor.

27. The system of claim 1, wherein the carrier signal is one among the following group: an RF carrier signal; a light carrier signal; or an audio carrier signal.

28. The system of claim 1, further comprising a chime, coupled to the external communication device, and configured to inform the patient to initiate communication between the external communication device and the internal communication device.

29. A method of communicating between the skin of a patient, comprising the steps of:

implanting an internal communication device inside the body of a patient;

transmitting a carrier signal into the body of the patient during communication from the internal communication device to an external communication device;

modulating the carrier signal inside the body of the patient with information by selectively reflecting the carrier signal or not reflecting the carrier signal the modulating step further comprising the steps of modulating the carrier signal with information of a first state during a first time interval during which the carrier signal is reflected and modulating the carrier signal with information of a second state during a second time interval during which the carrier signal is not reflected; and demodulating the information from the carrier signal by detecting when the carrier signal is reflected and when the carrier signal is not reflected outside the body of the patient.

30. The method of claim 29, wherein the modulating step further comprises the step of designating the first time interval and the second time interval to be substantially the same length in duration.

31. The method of claim 29, wherein the modulation step further comprising the step of reflecting the carrier signal when modulating the carrier signal with the information of a first state.

32. The method of claim 29, wherein the modulation step further comprising the step of not reflecting the carrier signal when modulating the carrier signal with the information of a second state.

33. The method of claim 29, further comprising the step of transmitting the information to a processing station.

34. The method of claim 33, further comprising the step of sending control information from the processing station to the internal communication device inside the body of a patient.

* * * * *